United States Patent
Chen et al.

(10) Patent No.: US 11,299,451 B2
(45) Date of Patent: Apr. 12, 2022

(54) METHOD FOR SYNTHESIZING 2-(1-CYCLOHEXENYL)ETHYLAMINE

(71) Applicant: Fudan University, Shanghai (CN)

(72) Inventors: Fener Chen, Shanghai (CN); Dang Cheng, Shanghai (CN); Zedu Huang, Shanghai (CN); Zhining Li, Shanghai (CN); Meifen Jiang, Shanghai (CN); Yuan Tao, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 16/953,317

(22) Filed: Nov. 19, 2020

(65) Prior Publication Data

US 2022/0002224 A1    Jan. 6, 2022

(30) Foreign Application Priority Data

Jul. 1, 2020  (CN) .......................... 202010628038.9

(51) Int. Cl.
| C07C 209/62 | (2006.01) |
| C07C 17/013 | (2006.01) |
| C07C 29/38  | (2006.01) |

(52) U.S. Cl.
CPC .......... *C07C 209/62* (2013.01); *C07C 17/013* (2013.01); *C07C 29/38* (2013.01); *C07C 2601/16* (2017.05)

(58) Field of Classification Search
None
See application file for complete search history.

(56) References Cited

FOREIGN PATENT DOCUMENTS

| CN | 105669465 A | 6/2016 |
| CN | 105859566 A | 8/2016 |
| CN | 108558673 A | 9/2018 |
| CN | 108821978 A | 11/2018 |
| CN | 107011178 B | 3/2019 |

OTHER PUBLICATIONS

Song Chang-sheng, Wu Bao-ping,Wu Qing-li, Jiao Guang-jun , Li Shu-an;Syn thesis of 1-cyclohex-1-en-1-ethylamine from cyclohex-1-en-1-aceton itr ile;App lied Chemical Industry,2005, 34(08): 484-486.

Kukula P, Gabova V, Koprivova K, et al. ;Selective hydrogenation of unsaturated nitriles to unsaturated amines over amorphous CoB and NiB alloys doped with chromium;Catalysis Today, 2007, 121(1-2):27-38.

(Continued)

*Primary Examiner* — Sudhakar Katakam
*Assistant Examiner* — Jennifer C Sawyer

(57) ABSTRACT

A method for synthesizing 2-(1-cyclohexenyl)ethylamine. Cyclohexanone (II) is reacted with a Grignard reagent in a first organic solvent to produce 1-vinylcyclohexanol (III), which is then subjected to chlorination and rearrangement reaction with a chlorinating reagent in a second organic solvent in the presence of an organic base to synthesize (2-chloroethylmethylene)cyclolxane (IV). Then (2-chloroethylmethylene)cyclohexane (IV) and urotropine are subjected to quaternization in a third organic solvent to synthesize N-cyclohexylidene ethyl urotropine hydrochloride (V). Finally, the N-cyclohexylidene ethyl urotropine hydrochloride (V) undergoes hydrolysis and rearrangement reaction in a solvent in the presence of an inorganic mineral acid to synthesize 2-(1-cyclohexenyl)ethylamine (I).

15 Claims, 4 Drawing Sheets

(56) References Cited

OTHER PUBLICATIONS

Hongyu Wang, Yunquan Man, Yanan Xiang, et al. ;Regioselective intramolecular Markovnikov and anti-Markovnikov hydrofunctionalization of alkenes via photoredox catalysis; Chem. Commun., 2019, 55: 11426-11429.

O. Schnider and J. Hellerbach;Synthese von Morphinanen; Helv. Chim. Acta, 1950, 33: 1437-1448.

METHOD FOR SYNTHESIZING 2-(1-CYCLOHEXENYL)ETHYLAMINE

CROSS-REFERENCE TO RELATED APPLICATIONS

This application claims the benefit of priority from Chinese Patent Application No. 202010628038.9, filed on Jul. 1, 2020. The content of the aforementioned application, including any intervening amendments thereto, is incorporated herein by reference in its entirety.

TECHNICAL FIELD

The present application relates to organic chemistry, and more particularly to a method for synthesizing 2-(1-cyclohexenyl)ethylamine.

BACKGROUND 2-(1-cyclohexenyl) ethylamine (CAS No: 3399-73-3) has the chemical structure shown in formula (I), and is an important intermediate in the synthesis of dextromethorphan hydrobromide.

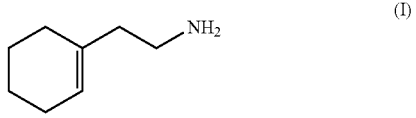

(I)

Chinese Patent No. 107011178B and Chinese Patent Application Publication No. 108558673A disclosed a method for preparing compound (I), respectively, by using modified Pd/C catalyst and Raney nickel for selective catalytic hydrogenation of 2-(1-cyclohexenyl)acetonitrile, but these methods generally suffered from poor regioselectivity, excessive by-products, difficult separation of the product from the reaction mixture in the downstream postprocessing and low yield, etc. Chinese Patent Application Publication No. 105669465A disclosed another method for preparing compound (I), in which 2-(1-cyclohexenyl)acetonitrile was hydrogenated at 1200-1300° C. under the catalysis of one or two of noble metals including hafnium, vanadium, and niobium. This method was carried out under harsh reaction conditions such as high temperature, resulting in high energy consumption. Chinese Patent Application Publication No. 108821978A disclosed a method for preparing compound (I) by catalytically hydrogenating 2-(1-cyclohexenyl)acetonitrile in a Vitride solution, which proclaimed a high yield, but the catalyst used therein was expensive, limiting the industrial application of this method. Chinese Patent Application Publication No. 105859566A disclosed a synthetic method for the compound (I), including: reacting 2-(1-cyclohexenyl) acetonitrile with 30-45% hydrobromic acid to produce 1-bromocyclohexyl acetonitrile; catalytically hydrogenating 1-bromocyclohexyl acetonitrile in the presence of palladium-nickel alloy; and dehydrating the hydrogenated product with an alkaline reagent to give the compound (I). But the hydrobromic acid used in this method is highly corrosive.

Kukula, et al. (Kukula P, Gabova V, Koprivova K, et al. Selective hydrogenation of unsaturated nitriles to unsaturated amines over amorphous CoB and NiB alloys doped with chromium[J]. *Catalysis Today,* 2007, 121(1-2):27-38.) reported a synthetic method for the compound (I), in which 2-(1-cyclohexenyl) acetonitrile was selectively hydrogenated under the catalysis of chromium-doped cobalt boride-nickel boride catalyst at 80 bar and 100° C. to produce the compound (I). However, the catalyst had a complex preparation procedure, and this method had high safety risk due to the need of high-pressure and high-temperature conditions, and low yield. It has been reported by Song, et al. (Changsheng Song et al. Synthesis of 1-cyclohex-1-en-1-ethylamine from cyclohex-1-en-1-acetonitrile. *Applied Chemical Industry,* 2005, 34(08):484-486.) that 2-(1-cyclohexenyl)acetonitrile, as a starting material, was hydrolyzed, acylchlorinated, and reduced to afford 2-(1-cyclohexenyl) ethanol, then the 2-(1-cyclohexenyl)ethanol underwent chlorination and amination with ammonia gas to produce compound (I). Obviously, this method had excessive synthetic steps and high cost. In the preparation proposed by Wang, et al. (Hongyu Wang, Yunquan Man, Yanan Xiang, et al. Regioselective intramolecular Markovnikov and anti-Markovnikov hydrofunctionalization of alkenes via photoredox catalysis[J]. *Chem. Commun,* 2019, 55: 11426-11429), cyclohexanone and cyanoacetic acid were condensed and decarboxylated to afford 2-(1-cyclohexenyl) acetonitrile, which further underwent chemical reduction to produce compound (I). This method requires expensive lithium aluminum hydride, limiting the industrial application. Schnider, et al. (O. Schnider and J. Hellerbach, Synthese von Morphinanen[J], *Helv. Chim. Acta,* 1950, 33: 1437-1448) reported a method for synthesis of the compound (I), in which the starting material cyclohexanone underwent Grignard reaction, dehydration and hydrolysis in succession to obtain the key intermediate cyclohexenyl acetic acid. It was then converted into the compound (I) via acylchlorination, amination and chemical reduction. This method involved a complicated synthetic route, and still used the expensive aluminum lithium hydride as the reducing agent, resulting in high production cost.

SUMMARY

An object of the present disclosure is to provide a method for synthesizing 2-(1-cyclohexenyl)ethylamine (I) with simple operation, low cost and high yield to overcome the shortcomings of the prior art.

Technical solutions of the disclosure are described as follows.

The disclosure provides a method for synthesizing 2-(1-cyclohexenyl)ethylamine of formula (I):

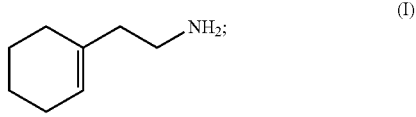

(I)

comprising:

(1) reacting cyclohexanone (II) with a Grignard reagent in a first organic solvent to produce 1-vinylcyclohexanol (III);

(2) subjecting 1-vinylcyclohexanol (III) to chlorination and rearrangement reaction with a chlorinating reagent in a second organic solvent in the presence of an organic base to synthesize (2-chloroethylmethylene)cyclohexane (IV);

(3) subjecting (2-chloroethylmethylene)cyclohexane (IV) and urotropine to quaternization in a third organic solvent to synthesize N-cyclohexylidene ethyl urotropine hydrochloride (V); and (4) subjecting the N-cyclohexylidene ethyl urotropine hydrochloride (V) to hydrolysis and rearrangement in a solvent in the presence of an inorganic mineral acid to produce 2-(1-cyclohexenyl)ethylamine (I); as shown in the following scheme:

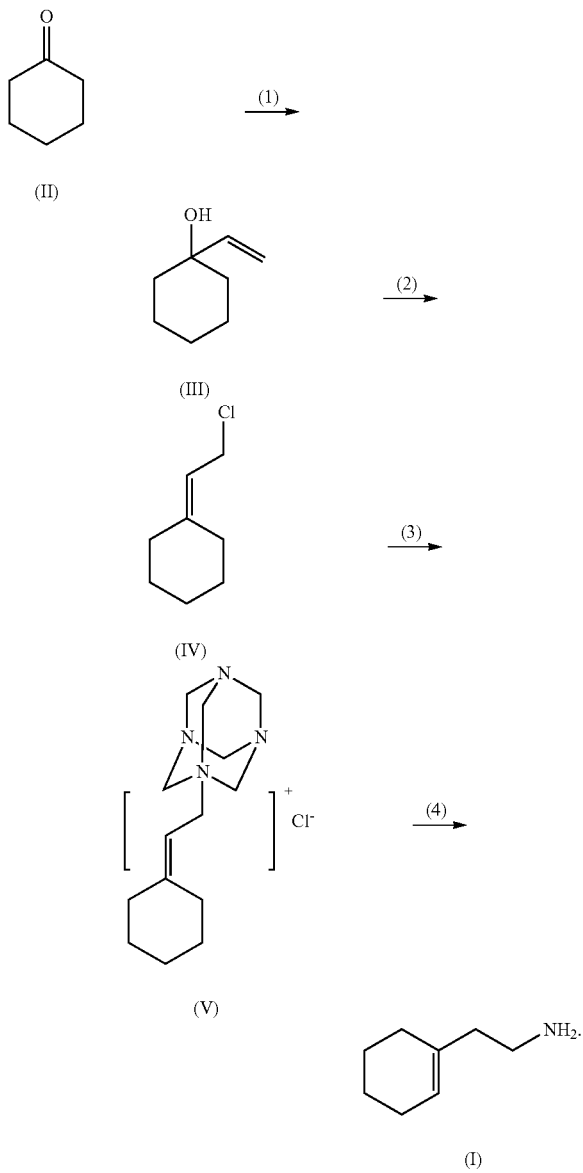

In some embodiments, wherein in step (1),
the Grignard reagent is vinyl magnesium bromide, vinyl magnesium chloride or vinyl magnesium iodide;
the first organic solvent is tetrahydrofuran or an alkyl ether; a molar ratio of the cyclohexanone (II) to the Grignard reagent is 1:1-3; and
the reaction is performed at −10° C.-40° C.
In some embodiments, wherein in step (2),
the organic base is a $C_1$-$C_5$ alkylamine or a pyridine compound; the chlorinating reagent is thionyl chloride, phosphorus oxychloride, phosphorus trichloride, phosphorus pentachloride or acetyl chloride;
the second organic solvent is tetrahydrofuran, dichloromethane, 1,4-dioxane, alkyl ethers, toluene, or a combination thereof;

a molar ratio of the 1-vinylcyclohexanol (III) to the organic base is 1:0.05-3.0; a molar ratio of the 1-vinylcyclohexanol (III) to the chlorinating reagent is 1:1.1-3.5; and
the chlorination and rearrangement reaction is performed at −10° C.-25° C.
In some embodiments, wherein in step (3),
a molar ratio of the (2-chloroethylmethylene)cyclohexane (IV) to urotropine is 1:1.0-3.0;
the third organic solvent is tetrahydrofuran, dichloromethane, 1,4-dioxane, or a combination thereof; and
the quaternization is performed at 30° C.-80° C.
In some embodiments, wherein in step (4),
the inorganic mineral acid is hydrochloric acid, sulfuric acid or nitric acid;
the solvent is water or a mixture of water and a low molecular weight alcohol; and
the hydrolysis and rearrangement reaction is performed at 40° C.-100° C.
In some embodiments, wherein in step (1),
the Grignard reagent is vinyl magnesium bromide or vinyl magnesium chloride;
the first organic solvent is tetrahydrofuran or isopropyl ether;
a molar ratio of the cyclohexanone (II) to the Grignard reagent is 1:1.2-1.6; and
the reaction is performed at −5° C.-20° C.
In some embodiments, wherein in step (2),
the organic base is a triethylamine or a pyridine;
the chlorinating reagent is thionyl chloride or phosphorus oxychloride;
the second organic solvent is tetrahydrofuran or dichloromethane;
a molar ratio of the 1-vinylcyclohexanol (III) to the organic base is 1:1.3-2.2;
a molar ratio of the 1-vinylcyclohexanol (III) to the chlorinating reagent is 1:1.2-1.8; and
the chlorination and rearrangement reaction is performed at 0° C.-15° C.;
In some embodiments, wherein in step (3),
a molar ratio of the (2-chloroethylmethylene)cyclohexane (IV) to urotropine is 1:1.02-1.1;
the third organic solvent is dichloromethane; and
the quaternization is performed at 40° C.-60° C.;
In some embodiments, wherein in step (4),
the inorganic mineral acid is hydrochloric acid;
the solvent is a mixture of water and ethanol; and
the hydrolysis and rearrangement reaction is performed at 60° C.-80° C.
Compared to the prior art, the method for synthesizing 2-(1-cyclohexenyl)ethylamine (I) of the invention has readily-available raw materials, mild reaction conditions, simple operation, low cost and high yield and purity, and thus it has a promising application prospect.

DETAILED DESCRIPTION OF EMBODIMENTS

Figure 1:
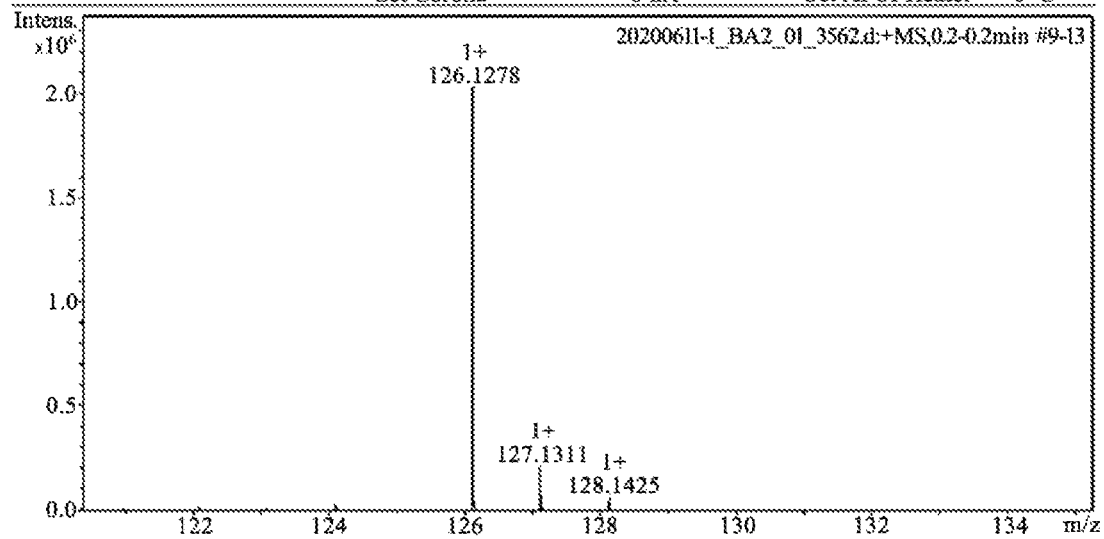
FIG. 1 is a high resolution mass spectrum (HRMS) of the target product 2-(1-cyclohexenyl)ethylamine (I) prepared in Example 9 of the present disclosure.
Figure 1:
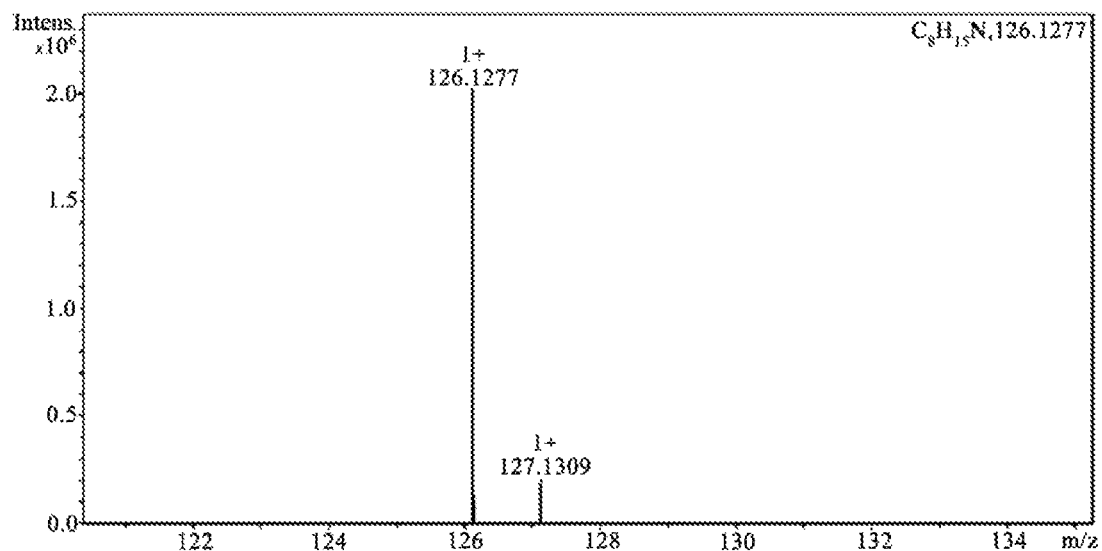
Figure 2:
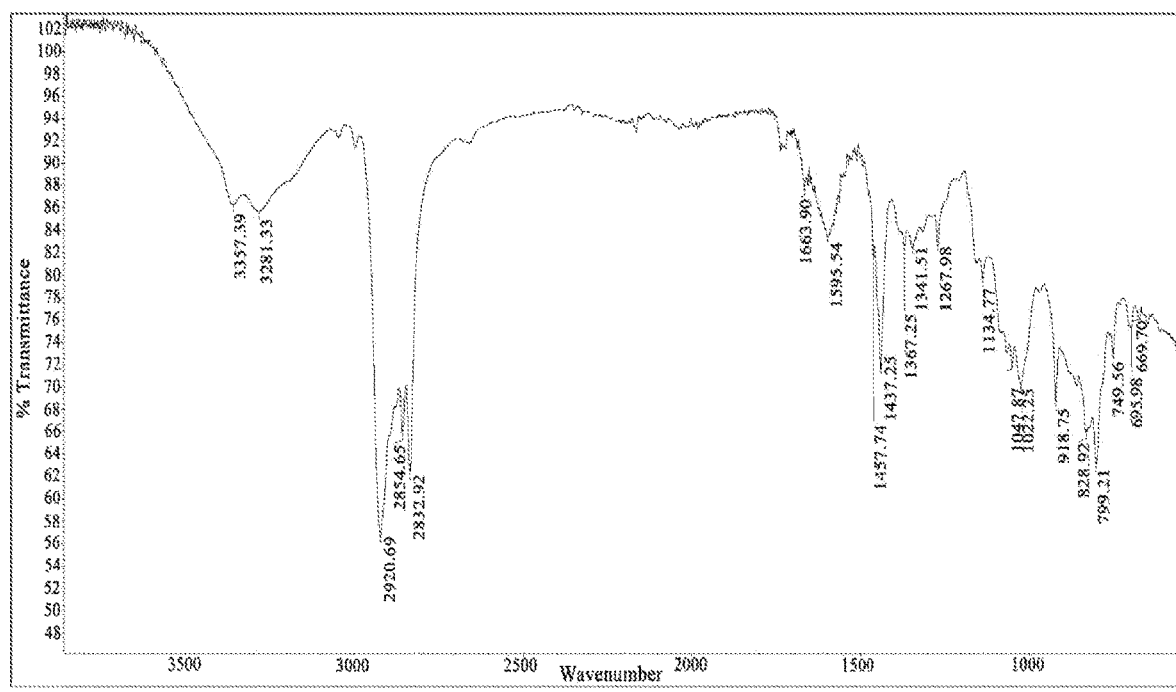
FIG. 2 is an infrared spectrum (IR) of the target product 2-(1-cyclohexenyl)ethylamine (I) prepared in Example 9 of the present disclosure.
Figure 3:
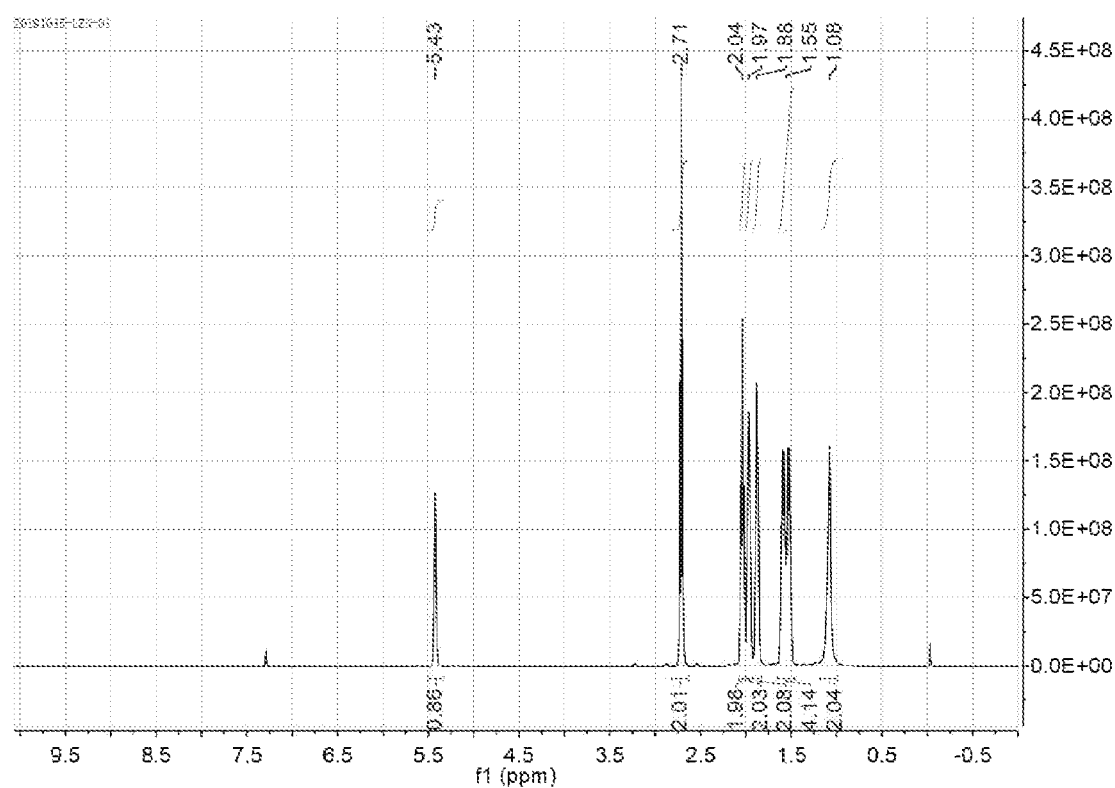
FIG. 3 is a $^1$H-NMR spectrum of the target product 2-(1-cyclohexenyl)ethylamine (I) prepared in Example 9 of the present disclosure.
Figure 4:
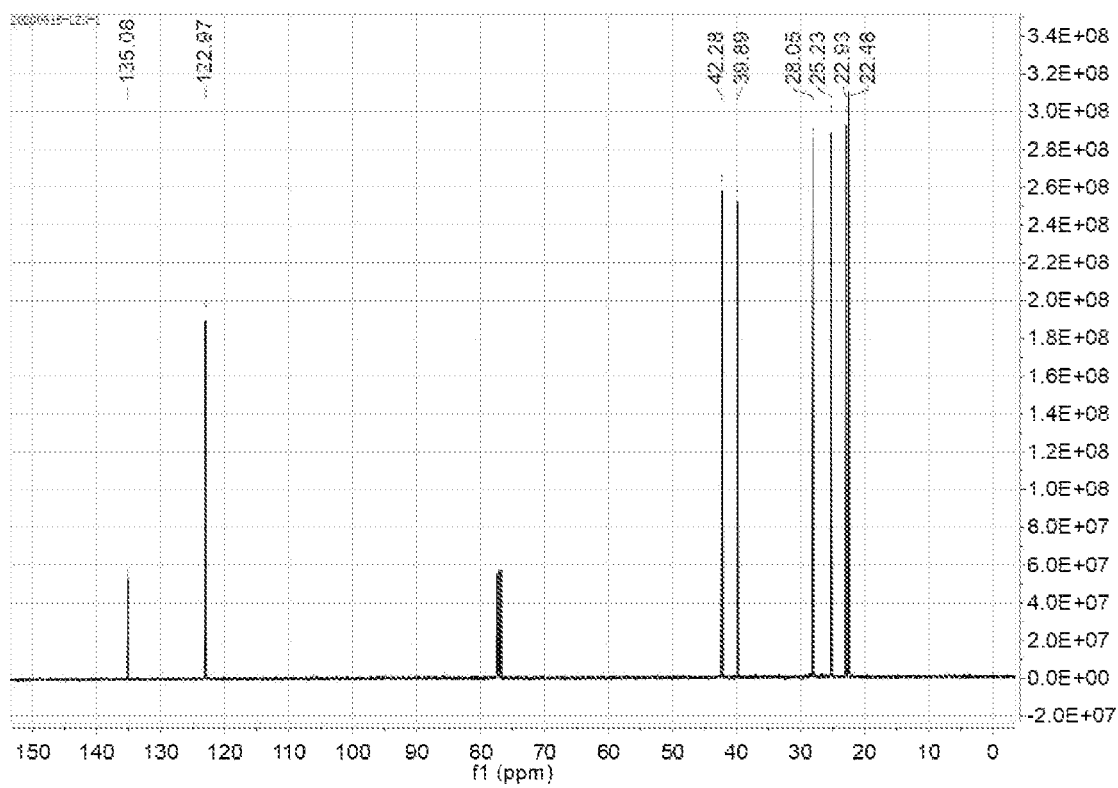
FIG. 4 is a $^{13}$C-NMR spectrum of the target product 2-(1-cyclohexenyl)ethylamine (I) prepared in Example 9 of the present disclosure.

The disclosure will be described in detail below in conjunction with embodiments and accompanying drawings to make the technical content, features, objects and advantages of the technical solution of the invention clearer. It should be understood that these embodiments are merely illustrative of the invention, and are not intended to limit the invention.

The present disclosure provides a method for synthesizing 2-(1-cyclohexenyl)ethylamine of formula (I):

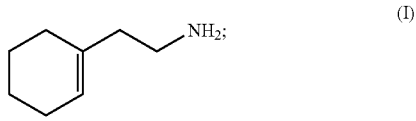

the method including:

(1) reacting cyclohexanone (II) with a Grignard reagent in a first organic solvent to produce 1-vinylcyclohexanol (III);

(2) subjecting 1-vinylcyclohexanol (III) to chlorination and rearrangement with a chlorinating reagent in a second organic solvent in the presence of an organic base to synthesize (2-chloroethylmethylene)cyclohexane (IV);

(3) subjecting, (2-chloroethylmethylene)cyclohexane (IV) and urotropine to quaternization in a third organic solvent, to synthesize N-cyclohexylidene ethyl urotropine hydrochloride (V); and (4) subjecting the N-cyclohexylidene ethyl urotropine hydrochloride (V) to hydrolysis and rearrangement in a solvent in the presence of inorganic mineral acid to prodece 2-(1-cyclohexenyl)ethylamine (I); as shown in the following scheme:

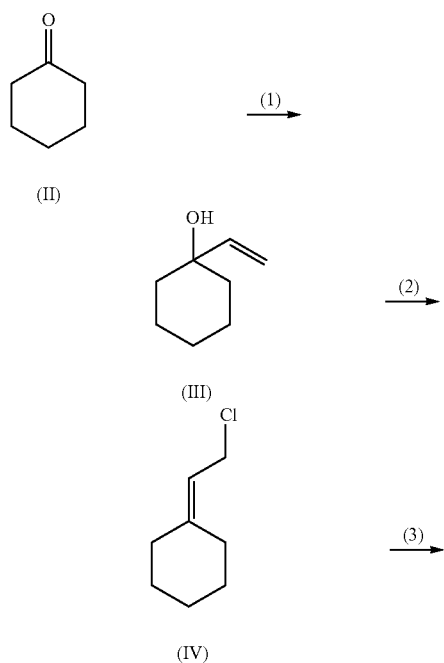

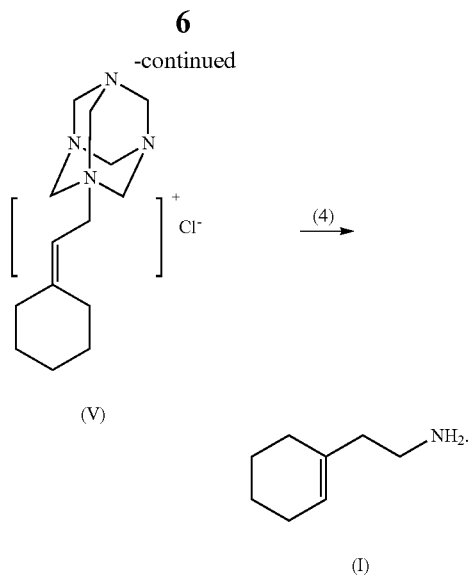

In some embodiments, in step (1), the Grignard reagent is vinylmagnesium bromide, vinylmagnesium chloride or vinylmagnesium iodide; a molar ratio of the cyclohexanone (II) to the Grignard reagent is 1:1-3. Preferably, the Grignard reagent is vinylmagnesium bromide or vinylmagnesium chloride; and the molar ratio of the cyclohexanone (II) to the Grignard reagent is 1:1.2-1.6.

In some embodiments, in step (1), the first organic solvent is tetrahydrofuran or an alkyl ether such as diethyl ether, isopropyl ether and methyl tert-butyl ether. Preferably, the first organic solvent is tetrahydrofuran or isopropyl ether, which has low cost and a wide range of sources, and can be easily recycled.

In some embodiments, in step (1), the Grignard reaction is performed at −10° C.-40° C., preferably −5° C.-20° C.

In some embodiments, in step (2), the organic base is a $C_1$-$C_5$ alkylamine or a pyridine compound; a molar ratio of the 1-vinylcyclohexanol (III) to the organic base is 1:0.05-3.0. Preferably, the organic base is triethylamine or pyridine; and the molar ratio of the 1-vinylcyclohexanol (III) to the organic base is 1:1.3-2.2.

In some embodiments, in step (2), the chlorinating reagent is thionyl chloride, phosphorus oxychloride, phosphorus trichloride, phosphorus pentachloride or acetyl chloride, which makes for mild reaction and high yield; and a molar ratio of the 1-vinylcyclohexanol (III) to the chlorinating reagent is 1:1.1-3.5. Preferably, the chlorinating reagent is thienyl chloride or phosphorus oxychloride; and the molar ratio of the 1-vinyl cyclohexanol (III) to the chlorinating reagent is 1:1.2-1.8.

In some embodiments, in step (2), the second organic solvent is tetrahydrofuran, dichloromethane, 1,4-dioxane, alkyl ethers, toluene, or a combination thereof, preferably tetrahydrofuran or dichloromethane.

In some embodiments, in step (2), the chlorination and rearrangement reaction is performed at −10° C.-25° C., preferably 0° C.-15° C.

In some embodiments, in step (3), a molar ratio of (2-chloroethylmethylene)cyclohexane (IV) to urotropine is 1:1.0-3.0, preferably 1:1.02-1.1.

In some embodiments, in step (3), the third organic solvent is tetrahydrofuran, dichloromethane, 1,4-dioxane, or a combination thereof, preferably dichloromethane.

In some embodiments, in step (3), the quaternization reaction is performed at 30° C.-80° C., preferably 40° C.-60° C.

In some embodiments, in step (4), the inorganic mineral acid is hydrochloric acid, sulfuric acid or nitric acid, preferably hydrochloric acid, which can lead to improved purity.

In some embodiments, in step (4), the solvent is water or a mixture of water and a low molecular weight alcohol such as methanol, ethanol, propanol and isopropanol. Preferably, the solvent is a mixture of water and ethanol in any volume ratio.

In some embodiments, in step (4), the hydrolysis and rearrangement reaction is performed at 40° C.-100° C., preferably 60° C.-80° C.

Compared to the prior art, the method for synthesizing 2-(1-cyclohexenyl)ethylamine (I) of the invention has readily available raw materials, mild reaction conditions, simple operation, low cost and high yield and purity, and thus it has a promising application prospect.

Detailed description will be given below in conjunction with embodiments. It should be noted that unless otherwise specified, the materials and reagents used in the following embodiments are all commercially available.

Example 1

Preparation of 1-Vinylcyclohexanol (III)

9.8 g of cyclohexanone (II) (0.1 mol) was mixed with 200 mL of tetrahydrofuran to obtain a mixture. Then the mixture was cooled to 0° C. in an ice bath and added with 100 mL of a solution of vinylmagnesium chloride in tetrahydrofuran (1.6 mol/L). The reaction mixture was heated to room temperature, reacted under stirring for 10 hours and quenched with a saturated ammonium chloride solution. An organic phase was collected, and an aqueous phase was subjected to extraction twice with ethyl acetate. The organic phases were combined and concentrated to obtain 12.4 g of crude product of 1-vinylcyclohexanol (III).

Example 2

Preparation of 1-Vinylcyclohexanol (III)

9.8 g of cyclohexanone (II) (0.1 mol) was mixed with 200 mL, of tetrahydrofuran to obtain a mixture. Then the mixture was cooled to 0° C. in an ice bath and added with 150 mL of a solution of vinyl magnesium bromide in tetrahydrofuran (1 mol/L). The reaction mixture was heated to room temperature, reacted under stirring for 6 hours and quenched with a saturated ammonium chloride solution. An organic phase was collected, and an aqueous phase was subjected to extraction twice with ethyl acetate. The organic phases were combined and concentrated to obtain 12.6 g of crude product of 1-vinylcyclohexanol (III).

Example 3

Preparation of 1-Vinylcyclohexanol (III)

9.8 g of cyclohexanone (II) (0.1 mol) was mixed with 200 mL of tetrahydrofuran to obtain a mixture. Then the mixture was cooled to 0° C. in an ice bath and added with 300 mL of a solution of vinyl magnesium bromide in isopropyl ether (0.5 mol/L). The reaction mixture was heated to room temperature, reacted under stirring for 6 hours and quenched with a saturated ammonium chloride solution. An organic phase was collected, and an aqueous phase was subjected to extraction twice with ethyl acetate. The organic phases were combined and concentrated to obtain 12.5 g of crude product of 1-vinylcyclohexanol (III).

Example 4

Preparation of (2-Chloroethylmethylene)Cyclohexane (IV)

12.6 g of 1-vinylcyclohexanol (III) (0.1 mol) prepared in Example 2 was mixed with 150 mL of tetrahydrofuran to obtain a mixture. Then the mixture was cooled to 0° C. in an ice bath and sequentially added with 14.22 g of pyridine (0.18 mol) and 18.88 g of thionyl chloride (0.16 mol). The reaction mixture was reacted under stirring for 45 min and then quenched with a saturated NaHCO$_3$ solution. An organic phase was collected, and an aqueous phase was subjected to extraction twice with ethyl acetate. The organic phases were combined and distilled under vacuum to obtain 11.23 g of oily liquid (2-chloroethylmethylene)cyclohexane (IV).

Example 5

Preparation of (2-Chloroethylmethylene)Cyclohexane (IV)

12.6 g of 1-vinylcyclohexanol (III) (0.1 mol) prepared in Example 2 was mixed with 200 mL of dichloromethane to obtain a mixture. Then the mixture was cooled to 0° C. in an ice bath and sequentially added with 10.1 g of triethylamine (0.1 mol) and 35.4 g of thionyl chloride (0.3 mol). Then the reaction mixture was gradually heated to a reflux temperature (40° C.), reacted under stirring for 4 h and quenched with a saturated NaHCO$_3$ solution, where the reflux temperature was the temperature at which the liquid components in the reaction system was refluxed or in a boiling state. An organic phase was collected, and an aqueous phase was subjected to extraction twice with ethyl acetate. The organic phases were combined and distilled under vacuum to obtain 9.25 g of oily liquid (2-chloroethylmethylene)cyclohexane (IV).

Example 6

Preparation of N-Cyclohexylidene Ethyl Urotropine Hydrochloride (V)

11.23 g of (2-chloroethylmethylene) cyclohexane (IV) (0.078 mol) prepared in Example 4 was mixed with 150 mL of dichloromethane, to which 11.26 g of urotropin (0.080 mol) was added. Then the reaction mixture was refluxed at 40° C. overnight and filtered while it was hot. The resulting filter cake was washed with a small amount of dichloromethane and dried to obtain 17.89 g of white solid N-cyclohexylidene ethyl urotropin hydrochloride (V). The preparation of N-cyclohexylidene ethyl urotropin hydrochloride (V) from cyclohexanone (II) through Grignard reaction in Example 2, the chlorination/rearrangement reaction in Example 4 and the quaternization described herein had a yield of 63%.

Example 7

Preparation of N-Cyclohexylidene Ethyl Urotropine Hydrochloride (V)

11.23 g of (2-chloroethylmethylene) cyclohexane (IV) (0.078 mol) prepared in Example 4 was mixed with 150 mL of tetrahydrofuran, to which 11.26 g of urotropin (0.080 mol) was added. The reaction mixture was reacted at 60° C. for 12 h and filtered. The resulting filter cake was washed with a small amount of dichloromethane and dried to obtain 19.35 g of white solid N-cyclohexylidene ethyl urotropin hydrochloride (V). The preparation of N-cyclohexylidene ethyl urotropin hydrochloride (V) from cyclohexanone (II) through Grignard reaction in Example 2, the chlorination/rearrangement reaction in Example 4 and the quaternization described herein had a yield of 68%.

Example 8

Preparation of 2-(1-Cyclohexenyl)Ethylamine (I)

5.00 g of N-cyclohexylidene ethyl urotropin hydrochloride (V) (0.018 mol) prepared in Example 7 was mixed with 30 mL of absolute ethanol, to which 10 mL of concentrated hydrochloric acid (37%) was added under stirring. The reaction mixture was heated to 80° C. and reacted for 5 h. The reaction mixture was cooled and filtered, and the filtrate was collected and subjected to extraction with ethyl ether once. Then the filtrate was adjusted to pH 12 and subjected to extraction twice with ethyl ether. The organic phases were collected, combined and concentrated to obtain 1.80 g of target 2-(1-cyclohexenyl) ethylamine (I) (80% yield).

Example 9

Preparation of 2-(1-Cyclohexenyl)Ethylamine (I)

5.00 g of N-cyclohexylidene ethyl urotropin hydrochloride (V) (0.018 mol) prepared in Example 7 was dissolved in 10 mL of water, to which 10 mL of 4 mol/L, hydrochloric acid was added under stirring. The reaction mixture was heated to 100° C. and reacted for 3 h. The reaction mixture was cooled and filtered, and the filtrate was collected and subjected to extraction with ethyl ether once. Then the filtrate was adjusted to pH 12, and subjected to extraction twice with ethyl ether. The organic phases were collected, combined and concentrated to obtain 1.68 g of the target product 2-(1-cyclohexenyl)ethyl amine (I) (75% yield).

The target product 2-(1-cyclohexenyl)ethylamine (I) prepared in Example 9 was collected, and analyzed respectively by high-resolution mass spectrometry (HRMS), infrared absorption spectroscopy (IR) and nuclear magnetic resonance spectroscopy (NMR), and the results were specifically listed as follows:

(1) HRMS (ESI$^+$): calculated for $C_8H_{15}N$ [M$^+$H]$^+$= 126.1277, found: 126.1278;

(2) IR: v 3357.39, 3281.33, 2920.69, 2854.65, 2832.92 cm$^{-1}$;

(3) $^1$H-NMR (400 MHz, CDCl$_3$): δ=5.43 (s, CH=C), 2.74 (t, 2H, J=6.7, CH$_2$NH$_2$), 2.04 (t, 2H, J=6.5, NH$_2$), 1.96 (s, 2H, CH$_2$), 1.88 (s, 2H, CH$_2$), 1.69-1.42 (m, 4H, 2CH$_2$), 1.08 (s, 2H, CH$_2$); and (4) $^{13}$C-NMR (101 MHz, CDCl$_3$): δ=135.08, 122.97, 42.28, 39.89, 28.05, 25.23, 22.93, 22.48.

It should be noted that described above are merely preferred embodiments of the invention, which are not intended to limit the invention. Any modifications and changes made by those skilled in the art without deviating from the spirit of the invention should fall within the scope of the invention as defined by the appended claims.

What is claimed is:

1. A method for synthesizing 2-(1-cyclohexenyl)ethylamine of formula (I):

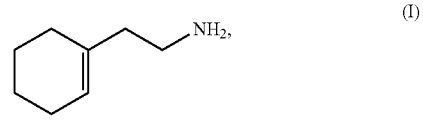

the method comprising:

(1) reacting cyclohexanone (II) with a Grignard reagent in a first organic solvent to produce 1-vinylcyclohexanol (III);

(2) subjecting 1-vinylcyclohexanol (III) to chlorination and rearrangement reaction with a chlorinating reagent in a second organic solvent in the presence of an organic base to synthesize (2-chloroethylmethylene)cyclohexane (IV);

(3) subjecting (2-chloroethylmethylene)cyclohexane (IV) and urotropine to quaternization in a third organic solvent to synthesize N-cyclohexylidene ethyl urotropine hydrochloride (V); and (4) subjecting the N-cyclohexylidene ethyl urotropine hydrochloride (V) to hydrolysis and rearrangement in a solvent in the presence of an inorganic mineral acid to produce 2-(1-cyclohexenyl)ethylamine (I); as shown in the following scheme:

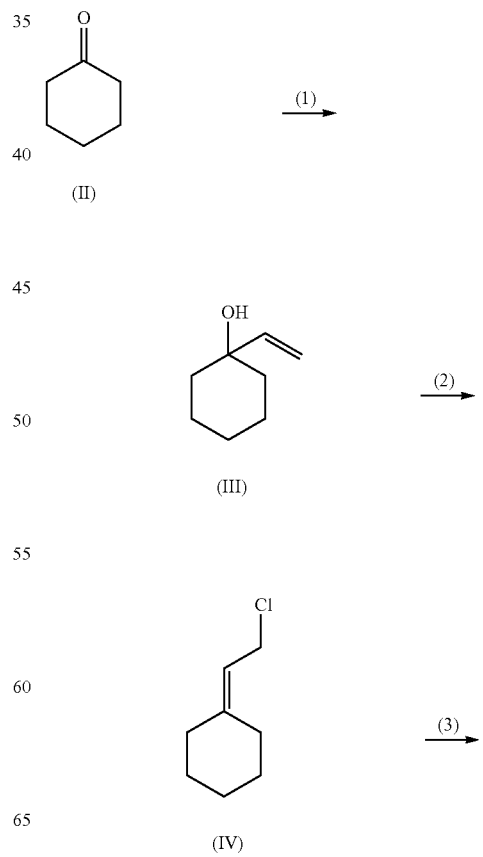

-continued

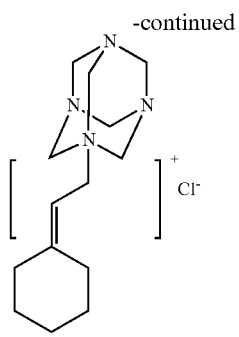

(V)

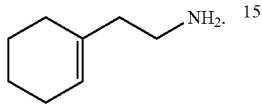

(I)

2. The method of claim 1, wherein in step (1),
the Grignard reagent is vinylmagnesium bromide, vinylmagnesium chloride or vinylmagnesium iodide;
the first organic solvent is tetrahydrofuran or an alkyl ether;
a molar ratio of the cyclohexanone (II) to the Grignard reagent is 1:1-3; and
the reaction is performed at −10° C.-40° C.

3. The method of claim 1, wherein in step (2),
the organic base is a $C_1$-$C_5$ alkylamine or a pyridine compound; the chlorinating reagent is thionyl chloride, phosphorus oxychloride, phosphorus trichloride, phosphorus pentachloride or acetyl chloride;
the second organic solvent is tetrahydrofuran, dichloromethane, 1,4-dioxane, alkyl ethers, toluene, or a combination thereof;
a molar ratio of the 1-vinylcyclohexanol (III) to the organic base is 1:0.05-3.0;
a molar ratio of the 1-vinylcyclohexanol (III) to the chlorinating reagent is 1:1.1-3.5; and
the chlorination and rearrangement reaction is performed at −10° C.-25° C.

4. The method of claim 1, wherein in step (3),
a molar ratio of the (2-chloroethylmethylene)cyclohexane (IV) to urotropine is 1:1.0-3.0;
the third organic solvent is tetrahydrofuran, dichloromethane, 1,4-dioxane, or a combination thereof; and
the quaternization is performed at 30° C.-80° C.

5. The method of claim 1, wherein in step (4),
the inorganic mineral acid is hydrochloric acid, sulfuric acid or nitric acid;
the solvent is water or a mixture of water and a low molecular weight alcohol; and
the hydrolysis and rearrangement reaction is performed at 40° C.-100° C.

6. The method of claim 1, wherein in step (1), the Grignard reagent is vinylmagnesium bromide, vinylmagnesium chloride or vinylmagnesium iodide; the first organic solvent is tetrahydrofuran or an alkyl ether; a molar ratio of the cyclohexanone (II) to the Grignard reagent is 1:1-3; the reaction is performed at −10° C.-40° C.;
in step (2), the organic base is a $C_1$-$C_5$ alkylamine or a pyridine compound; the chlorinating reagent is thionyl chloride, phosphorus oxychloride, phosphorus trichloride, phosphorus pentachloride or acetyl chloride; the second organic solvent is tetrahydrofuran, dichloromethane, 1,4-dioxane, alkyl ethers, toluene, or a combination thereof; a molar ratio of the 1-vinylcyclohexanol (III) to the organic base is 1:0.05-3.0; a molar ratio of the 1-vinylcyclohexanol (III) to the chlorinating reagent is 1:1.1-3.5; the chlorination and rearrangement reaction is performed at −10° C.-25° C.;
in step (3), a molar ratio of the (2-chloroethylmethylene) cyclohexane (IV) to urotropine is 1:1.0-3.0; the third organic solvent is tetrahydrofuran, dichloromethane, 1,4-dioxane, or a combination thereof; the quaternization is performed at 30° C.-80° C.; and
in step (4), the inorganic mineral acid is hydrochloric acid, sulfuric acid or nitric acid; the solvent is water or a mixture of water and a low molecular weight alcohol; and the hydrolysis and rearrangement reaction is performed at 40° C.-100° C.

7. The method of claim 2, wherein in step (1),
the Grignard reagent is vinylmagnesium bromide or vinylmagnesium chloride;
the first organic solvent is tetrahydrofuran or isopropyl ether;
the molar ratio of the cyclohexanone (II) to the Grignard reagent is 1:1.2-1.6; and
the reaction is performed at −5° C.-20° C.

8. The method of claim 3, wherein in step (2),
the organic base is triethylamine or pyridine;
the chlorinating reagent is thionyl chloride or phosphorus oxychloride;
the second organic solvent is tetrahydrofuran or dichloromethane;
the molar ratio of the 1-vinylcyclohexanol (III) to the organic base is 1:1.3-2.2;
the molar ratio of the 1-vinylcyclohexanol (III) to the chlorinating reagent is 1:1.2-1.8; and
the chlorination and rearrangement reaction is performed at 0° C.-15° C.

9. The method of claim 4, wherein in step (3),
the molar ratio of the (2-chloroethylmethylene)cyclohexane (IV) to urotropine is 1:1.02-1.1;
the third organic solvent is dichloromethane; and
the quaternization is performed at 40° C.-60° C.

10. The method of claim 5, wherein in step (4),
the inorganic mineral acid is hydrochloric acid;
the solvent is a mixture of water and ethanol; and
the hydrolysis and rearrangement reaction is performed at 60° C.-80° C.

11. The method of claim 6, wherein in step (1),
the Grignard reagent is vinylmagnesium bromide or vinylmagnesium chloride;
the first organic solvent is tetrahydrofuran or isopropyl ether;
the molar ratio of the cyclohexanone (II) to the Grignard reagent is 1:1.2-1.6; and
the reaction is performed at −5° C.-20° C.

12. The method of claim 6, wherein in step (2),
the organic base is triethylamine or pyridine;
the chlorinating reagent is thionyl chloride or phosphorus oxychloride;
the second organic solvent is tetrahydrofuran or dichloromethane;
the molar ratio of the 1-vinylcyclohexanol (III) to the organic base is 1:1.3-2.2;
the molar ratio of the 1-vinylcyclohexanol (III) to the chlorinating reagent is 1:1.2-1.8; and
the chlorination and rearrangement reaction is performed at 0° C.-15° C.

13. The method of claim 6, wherein in step (3),
the molar ratio of the (2-chloroethylmethylene)cyclohexane (IV) to urotropine is 1:1.02-1.1;
the third organic solvent is dichloromethane; and
the quaternization is performed at 40° C.-60° C.

14. The method of claim 6, wherein in step (4),
the inorganic mineral acid is hydrochloric acid;
the solvent is a mixture of water and ethanol; and
the hydrolysis and rearrangement reaction is performed at 60° C.-80° C.

15. The method of claim 6, wherein in step (1), the Grignard reagent is vinylmagnesium bromide or vinylmagnesium chloride; the first organic solvent is tetrahydrofuran or isopropyl ether; the molar ratio of the cyclohexanone (II) to the Grignard reagent is 1:1.2-1.6; and the reaction is performed at −5° C.-20° C.;

in step (2), the organic base is triethylamine or pyridine; the chlorinating reagent is thionyl chloride or phosphorus oxychloride; the second organic solvent is tetrahydrofuran or dichloromethane; the molar ratio of the 1-vinylcyclohexanol (III) to the organic base is 1:1.3-2.2; the molar ratio of the 1-vinylcyclohexanol (III) to the chlorinating reagent is 1:1.2-1.8; and the chlorination and rearrangement reaction is performed at 0° C.-15° C.;

in step (3), the molar ratio of the (2-chloroethylmethylene)cyclohexane (IV) to urotropine is 1:1.02-1.1; the third organic solvent is dichloromethane; and the quaternization is performed at 40° C.-60° C.; and in step (4), the inorganic mineral acid is hydrochloric acid; the solvent is a mixture of water and ethanol; and the hydrolysis and rearrangement reaction is performed at 60° C.-80° C.

* * * * *